United States Patent [19]

Ma

[11] 4,297,514
[45] Oct. 27, 1981

[54] METHOD OF OXIDIZING COMPOUNDS HAVING ACTIVATED METHYLENE RADICALS

[75] Inventor: King W. Ma, Midland, Mich.

[73] Assignee: The Dow Chemical Company, Midland, Mich.

[21] Appl. No.: 130,325

[22] Filed: Mar. 14, 1980

Related U.S. Application Data

[63] Continuation of Ser. No. 972,850, Dec. 26, 1978, abandoned.

[51] Int. Cl.$^3$ .................. C07C 45/36; C07C 45/28
[52] U.S. Cl. .................................. 568/321; 568/311; 568/309; 546/81; 546/82; 546/83; 546/89; 544/344; 260/326.9
[58] Field of Search ............... 568/321, 311, 309

[56] References Cited

U.S. PATENT DOCUMENTS

| | | | |
|---|---|---|---|
| 3,875,237 | 4/1975 | Nizik | 568/321 |
| 4,011,266 | 3/1977 | Pearson et al. | 568/321 |
| 4,218,400 | 8/1980 | Finger | 568/321 |

OTHER PUBLICATIONS

Hawthorne et al., Advances in Chem. Series, 75, pp. 14-20 (1968).
Yang, J. O. C., vol. 42, pp. 3754-3757 (1977).
Alveri et al., Tet. Letters, vol. 24, pp. 2117-2124 (1977).
Starks, J.A.C.S., vol. 93, pp. 195-199 (1971).

*Primary Examiner*—Natalie Trousof
*Assistant Examiner*—James H. Reamer
*Attorney, Agent, or Firm*—Charles J. Enright

[57] ABSTRACT

Compounds having activated methylene radicals are oxidized to various oxidation products by an improved process comprising contacting the compound with an oxidizing agent and a base of sufficient strength to deprotonate at least one hydrogen from the activated methylene radical in the presence of a catalytic amount of a synergistic combination of elemental carbon and a phase-transfer catalyst. For example, flourene is oxidized to flourenone by contacting the flourene with elemental oxygen and sodium hydroxide in the presence of a catalytic amount of the synergistic combination of charcoal and benzyltriethyl-ammonium chloride.

14 Claims, No Drawings

METHOD OF OXIDIZING COMPOUNDS HAVING ACTIVATED METHYLENE RADICALS

CROSS-REFERENCE TO RELATED APPLICATION

This is a continuation of application Ser. No. 972,850 filed Dec. 26, 1978, now abandoned.

BACKGROUND OF THE INVENTION

1. Field of the Invention

This invention relates to the oxidation of organic compounds. In one aspect, the invention relates to the oxidation of compounds having at least one activated methylene radical while in another aspect, the invention relates to oxidizing such a compound in a multiphase system employing a catalyst comprising a synergistic combination of elemental carbon and a phase-transfer catalyst.

2. Description of the Prior Art

Hawthorne et al., "Base-Catalyzed Autoxidation of 9,10-dihydroanthracene and Related Compounds", *Oxidation of Organic Compounds—I, Advances in Chemistry Series*, 75, 14 (ACS 1968) teach the oxidation of 9,10-dihydroanthracene to anthraquinone by contacting the dihydroanthracene with oxygen and benzyltrimethylammonium hydroxide. Pyridine was used as a solvent.

Kang Yang, *JOC*, 42, 3754 (1977), teaches the oxidation of fluorene to fluorenone in the presence of charcoal and a base. The base is potassium t-butoxide in either a t-butyl alcohol or sodium hydroxide solution.

Alveri et al., "Autoxidation of Diarylene Methanes and Related Compounds in the Presence of Phase-Transfer Catalysts", *Tetrahedron Letters*, 24, 2117 (1977), teach the use of a phase-transfer catalyst, e.g., dicetyl diethylammonium chloride, in the autoxidation of diarylene methanes. Fluorene was converted to fluorenone in 100 percent yield after 24 hours at 30° C. using the catalyst, oxygen and an aqueous sodium hydroxide/benzene biphasic reaction medium.

While all of the above teachings demonstrate utility, each suffers from one or more disadvantages. Principal among these disadvantages are undesirably slow reaction rates or the requirement of a neutralization step, the latter consuming starting reactants and generating a brine waste stream. Other disadvantages include the use of undesirable solvents, such as benzene, and the absence of catalyst and caustic recycle.

SUMMARY OF THE INVENTION

According to this invention, a method of oxidizing a compound of the formula

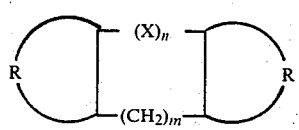

(I)

where
each R is the same or different, is

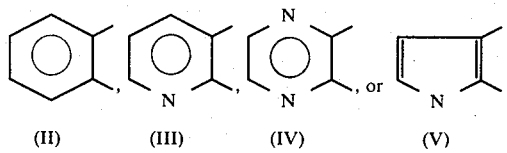

and each R can bear at least one inert substituent,
X is —$CH_2$—, O, S or N, and
m and n are individually zero or 1 with the proviso that m is 1 when either X is O, S or N or when n is zero, the method comprising contacting I with an oxidizing agent and a base of sufficient strength to deprotonate at least one hydrogen from a —$CH_2$— radical of I in the presence of a catalyst, is improved by using as the catalyst a synergistic combination of elemental carbon and a phase-transfer catalyst. This improved method exhibits a superior oxidation rate to the methods of the prior art and reduces or eliminates the generation of a brine waste stream. Moreover, the caustic solution, PTC and charcoal can be recycled and the product is facilely recovered from the reaction mixture.

DETAILED DESCRIPTION OF THE INVENTION

The compounds of this invention having at least one activated methylene radical are of formula I. Typically each R is the same and preferably either II or III. X is preferably —$CH_2$— or O although n is preferably zero. Each R can bear at least one substituent which is essentially nonreactive or inert toward the method reagents and products at method conditions. The substituent can either activate or deactivate R, although a deactivating substituent is most typical. Illustrative substituents include alkoxy, alkyl, aryl, nitro, amino, cyano, carboxyl, ester, carbonyl, halogen, etc. This invention is particularly useful in oxidizing fluorene (each R is II, n is zero and m is 1) to fluorenone.

Although conventional oxidizing agents such as hydrogen peroxide, ozone or persulfate ion are usable in this invention, elemental oxygen ($O_2$) supplied as ordinary air is satisfactory. The air and/or other oxidizing agent should be supplied in a quantity sufficient to furnish a small stoichiometric excess of oxygen over the amount of I to be oxidized.

Any base of sufficient strength to deprotonate at least one hydrogen from a —$CH_2$— radical of I can be used in the practice of this invention. "Deprotonate" here means to remove a hydrogen atom from the —$CH_2$— radical. Suitable bases include alkali and alkaline earth metal hydroxides, alkoxides, various amines, etc. The alkali and alkaline earth metal hydroxides are preferred with sodium and potassium hydroxide particularly preferred. Preferably, the minimum I:base mole ratio employed is about 1:1, and more preferably about 1.5:1. Practical limitations, such as convenience and economics, are the only limitations upon the maximum I:base mole ratio that can be used but a typical maximum is about 10:1 and preferably about 3:1 weight percent.

One component of the synergistic catalyst system of this invention is the phase-transfer catalyst. "Phase-transfer catalyst" here means any onium salt or crown ether capable of transporting the anion of a base from the aqueous phase across the interface into the organic phase of a multiphasic reaction mixture. Onium salts are preferred to the crown ethers and the quaternary ammonium and phosphonium salts are the preferred onium salts. These salts are described by Starks and Napier in British Pat. No. 1,227,144 and by Starks in JACS, 93, 195 (1971). Preferably, these onium salts have a minimum solubility of at least about 1 weight percent in both the organic phase and the aqueous phase at 25° C. The ammonium salts are preferred over the phosphonium salts and benzyltrimethyl-, benzyltriethyl-, tributylmethyl- and tetra-n-butylammonium chlorides and bromides are most preferred.

As a further illustration of the preferred type of ammonium and phosphonium salts here used, suitable such salts are represented by the formula

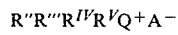 (II)

wherein $Q^+$ is a quaternized atom of nitrogen or phosphorus, $A^-$ is a neutralizing anion, and $R''$-$R^V$ are hydrocarbyl groups, i.e., alkyl, aryl, alkylaryl, cycloalkyl, etc., and $R''$ can join with $R'''$, or $R'''$ can join with $R^{IV}$, etc. to form a 5- or 6-membered heterocyclic compound having at least one quaternized nitrogen or phosphorus atom in the ring and they also can contain one nonadjacent atom of oxygen or sulfur within the ring. Typically, $R''$-$R^V$ are hydrocarbyl groups of from 1 to about 16 carbon atoms each with a combined minimum total of about 10 carbon atoms. Preferred onium salts have from about 10 to about 30 carbon atoms.

The neutralizing anion portion of the salt, i.e., $A^-$ in the above formula, can be varied to convenience. Chloride and bromide are the preferred anions, the other representative anions include fluoride, iodide, tosylate, acetate, bisulfate, etc. The following compounds serve as a further illustration: tetraalkylammonium salts, such as tetra-n-butyl-, tri-n-butylmethyl-, tetrahexyl-, trioctylmethyl-, hexadecyltriethyl-, and tridecylmethylammonium chlorides, bromides, iodides, bisulfates, tosylates, etc.; aralkyl ammonium salts, such as tetrabenzyl-, benzyltrimethyl-, benzyltriethyl-, benzyltributyl-, and phenethyltrimethylammonium chlorides, bromides, iodides, etc.; aryl ammonium salts, such as triphenylmethylammonium fluoride, chloride or bromide, N,N,N-trimethylanilinium chloride, N,N,N-triethylanilinium bromide, N,N-diethylanilinium bisulfate, trimethylnaphthylammonium chloride, p-methylphenyltrimethylammonium chloride or tosylate, etc.; 5- and 6-membered heterocyclic compounds containing at least one quaternary nitrogen atom in the ring, such as N,N-dibutylmorpholinium chloride, N-decylthiazolium chloride, etc. and the corresponding phosphonium salts.

The cocatalyst of the synergistic catalyst system of this invention is elemental carbon, i.e., carbon in one of its elemental forms, such as charcoal, graphite, carbon black, coke, activated carbon, etc. Particulate carbon, such as charcoal and activated carbon, are preferred. Moreover, the carbon can be admixed with other materials, such as silicates, carbonates, etc., or contain or support various oxidation catalysts, such as a transition metal or its oxide. Preferably the carbon is used free of such material.

The catalyst system of this invention comprises sufficient phase-transfer catalyst and elemental carbon to form a synergistic, catalytic combination. Typically, the composition ranges from a carbon:phase-transfer catalyst weight ratio of about 5:1 to about 20:1, and preferably from about 10:1 to about 15:1.

A catalytic amount of this synergistic combination is required for the practice of this invention. When practiced on a batch basis, a typical minimum amount, based upon the weight of I, is about 100 weight percent and preferably about 200 weight percent. As with the base, practical considerations are the only limitations upon the maximum amount of catalyst system that can be used but as a practical matter, a maximum amount of about 1,000 weight percent, and preferably of about 400 weight percent, is used. When the invention is practiced on a continuous basis, the carbon component of the catalyst system can be conveniently supplied as a fixed bed, while the phase-transfer catalyst component can be admixed with I prior to contacting I with the fixed bed of carbon. On such a basis, about 5 to about 20 and preferably about 10 to about 18 weight percent, based on I, of the phase-transfer catalyst is admixed with I.

The reaction mixture is multiphasic, typically biphasic. The base and the phase-transfer catalyst component of the catalyst system are generally in the aqueous phase while I is in the organic phase. The carbon is and remains a solid. If the compounds of I are liquid at room temperature, the reaction can be conducted neat, i.e., in the absence of an organic solvent. If the compounds of I are solid at room temperature, then they are preferably solubilized in an inert organic solvent, most typically halogenated aliphatics or aromatics. A hallmark of this invention is that it can be practiced with inexpensive, easy-to-use and generally environmentally safe solvents, such as methylene chloride or a dichlorobenzene. If the oxidizing agent is elemental oxygen or air, it can be sparged through the reaction mixture or form a blanket over an agitated reaction mixture in a pressurized reaction vessel.

Temperature and pressure are critical to this invention only to the extent that the multiphasic mixture of I, aqueous phase (water) and the phase-transfer catalyst component of the catalyst system remains a liquid. Best results are obtained when the reaction temperatures range from about 40° C. to about 110° C., preferably from about 60° C. and about 90° C. Atmospheric pressure is used as a matter of convenience but both sub- and superatmospheric pressure can be used.

A batch reaction mixture is typically agitated, either by stirring or shaking, throughout the reaction.

The various oxidation products of this invention will of course vary with both the starting materials and the degree of oxidation permitted. Alehydes, ketones and carboxylic acids are the principal products but sufficient oxidation can also produce alcohols. Fluorene is typically oxidized to fluorenone.

The oxidation products have a myriad of utility but are most useful in the preparation of polyesters and polycarbonates. Fluorenone in particular is useful in the preparation of high heat-resistant polycarbonates.

The following are illustrative embodiments of this invention. Unless indicated to the contrary, all parts and percentages are by weight.

SPECIFIC EMBODIMENTS

Example 1

A three-necked, 500 ml round bottom flask equipped with a high-speed stirrer and water-cooled condenser was charged with fluorene (4.5 g, 85% purity), sodium hydroxide (2 g), tributylmethylammonium chloride (0.75 g), charcoal (10 g), water (70 ml), and a dichlorobenzene (100 ml). The reaction mixture was stirred vigorously in the presence of one atmospheric pressure of oxygen for a period of 1½ to 2 hours at 65° C.–70° C.

Vapor phase chromatography of the organic phase revealed the formation of greater than 92 percent fluorenone. The authenticity of the fluorenone was established by coinjection and spectroscopic identification techniques. The reaction mixture was then filtered with a sintered glass funnel to separate the charcoal and a separatory funnel was used to separate the organic from the aqueous phase. Removal of the excess organic solvent by distillation gave about 3.3 g of crude fluorenone (approximately 80 percent yield).

Control A

The procedure of Example 1 was repeated without the phase-transfer catalyst. After approximately 3 hours of reaction, only approximately 9 percent fluorenone had been formed.

Control B

The procedure of Example 1 was repeated except charcoal was omitted. After 2 hours of reaction, less than 3 percent fluorenone had been formed.

Control C

The procedure of Example 1 was repeated except 5 percent palladium-on-charcoal (2 g) was substituted for the charcoal of Example 1. No major retarding or accelerating effect was observed.

Examples 2-4

The procedure of Example 1 was thrice repeated except that the charcoal, caustic and tributylmethylammonium chloride used was that recycled from Example 1. No appreciable effect on reaction rate or product yield was observed.

Example 5

9,10-Dihydroanthracene (5 g), sodium hydroxide (2.2 g), dichlorobenzene (100 ml), water (80 ml), charcoal (10 g) and tributylmethylammonium chloride (1 g) were charged to a three-necked, 500 ml round bottom flask equipped with a high-speed stirrer and a water-cooled condenser. The mixture was stirred vigorously for 15 hours in the presence of an atmospheric pressure of oxygen at about 70° C. Vapor phase chromatography of the organic phase revealed the formation of anthracene (~10%), anthrone (~20%) and anthraquinone (~15%).

Although the invention has been described in considerable detail by the above examples, the detail is provided for the purpose of illustration only and is not to be construed as a limitation upon the scope of the invention or the appended claims.

What is claimed is:

1. In a method for oxidizing fluorene to fluorenone comprising contacting fluorene with an oxidizing agent and an aqueous solution of a base of sufficient strength to deprotonate hydrogen from a —CH$_2$— radical of the fluorene in the presence of a catalyst, the improvement comprising using as the catalyst a synergistic combination of:
(1) a member from the group consisting of charcoal, graphite, carbon black, coke, activated carbon and mixtures thereof; and
(2) a phase transfer catalyst.

2. The method of claim 1 wherein the phase-transfer catalyst is a quaternary ammonium or phosphonium salt.

3. The method of claim 1 wherein the phase-transfer catalyst is of the formula $$R''R'''R^{IV}R^{V}Q^{+}A^{-} \qquad (VI)$$

wherein $Q^+$ is a quaternized atom of nitrogen or phosphorus, $A^-$ is a neutralizing anion, and $R''$-$R^V$ are hydrocarbyl groups of from 1 to 16 carbon atoms each with a combined minimum total of about 10 carbon atoms.

4. The method of claim 1 wherein the phase-transfer catalyst is benzyltrimethyl-, benzyltriethyl-, tributylmethy- or tetra-n-butylammonium chloride or bromide.

5. The method of claim 2 wherein the (1) is charcoal.

6. The method of claim 5 wherein the oxidizing agent is elemental oxygen.

7. The method of claim 6 wherein the base is an alkali or alkaline earth metal hydroxide.

8. The method of claim 7 wherein the charcoal and phase-transfer catalyst are present at a charcoal:phase-transfer catalyst weight ratio of about 5:1 to about 20:1.

9. The method of claim 8 wherein the synergistic combination, based upon the weight of fluorene, is present at a weight percent of about 100 to about 1,000.

10. The method of claim 9 wherein fluorene and the base are present at a fluorene:base mole ratio of about 1:1 to about 10:1.

11. The method of claim 10 wherein the oxidizing agent is present in a stoichiometric excess over the amount of fluorene.

12. The method of claim 11 wherein the contacting is conducted at a temperature of about 40° C. to about 90° C.

13. The method of claim 11 wherein fluorene is solubilized in methylene chloride or a dichlorobenzene.

14. A method of oxidizing fluorene to fluorenone, the method comprising contacting, as a multiphasic mixture and at a temperature of about 40° C. to about 90° C., fluorene dissolved in methylene chloride or a dichlorobenzene with a stoichiometric excess of elemental oxygen and an aqueous solution of an alkali metal hydroxide, the fluorene and alkali metal hydroxide present at a mole ratio of about 1:1 to about 10:1, in the presence of about 100 to about 1,000 weight percent of a catalyst, based on the weight of fluorene, the catalyst consisting of the synergistic combination of charcoal and a phase-transfer catalyst of the formula $$R''R'''R^{IV}R^{V}Q^{+}A^{-}$$

wherein $Q^+$ is a quaternized atom of nitrogen or phosphorus, $A^-$ is a halide or bisulfate anion, and $R''$-$R^V$ are hydrocarbyl groups of from 1 to 16 carbon atoms each with a combined minimum total of about 10 carbon atoms, the charcoal and phase-transfer catalyst present at a weight ratio of about 5:1 to about 20:1.

* * * * *

UNITED STATES PATENT AND TRADEMARK OFFICE
CERTIFICATE OF CORRECTION

PATENT NO. : 4,297,514
DATED : October 27, 1981
INVENTOR(S) : King W. Ma

It is certified that error appears in the above—identified patent and that said Letters Patent is hereby corrected as shown below:

Col. 4, line 46, "Alehydes" should read -- Aldehydes --.

Col. 6, line 20, Claim 4, line 3, "methy-" should read -- methyl- --.

Signed and Sealed this

Thirtieth Day of March 1982

[SEAL]

Attest:

*Attesting Officer*

GERALD J. MOSSINGHOFF

*Commissioner of Patents and Trademarks*